US00PP22966P2

(12) United States Plant Patent

Klemm et al.

(10) Patent No.: US PP22,966 P2

(45) Date of Patent: Aug. 14, 2012

(54) *DIASCIA* PLANT NAMED 'KLEDB10715'

(50) Latin Name: ***Diascia barberae* Hook**
Varietal Denomination: KLEDB10715

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,830

(22) Filed: Mar. 29, 2011

(51) Int. Cl.
*A01H 5/00* (2006.01)

(52) U.S. Cl. ..... Plt./425

(58) Field of Classification Search ..... Plt./425
See application file for complete search history.

*Primary Examiner* — Annette Para

(74) *Attorney, Agent, or Firm* — Jondle & Associates, P.C.

(57) ABSTRACT

A new *Diascia* plant named 'KLEDB10715' particularly distinguished by its large flowers and brilliant color and very good branching, is disclosed.

1 Drawing Sheet

Genus and species: *Diascia barberae* Hook.
Variety denomination: 'KLEDB10715'.

BACKGROUND OF THE NEW PLANT

The present invention comprises a new and distinct variety of *Diascia*, botanically known as *Diascia barberae* Hook, and hereinafter referred to by the variety name 'KLEDB10715'. The new variety resulted from a cross conducted in June 2007 in Stuttgart, Germany between the female parent, proprietary *Diascia* plant 'DB 2007 0101' (unpatented), and the male parent, proprietary *Diascia* plant 'DP1' (unpatented). A single plant selection was chosen for further evaluation and asexual propagation.

The new variety was first propagated via vegetative cuttings and in vitro propagation in May 2008 in Stuttgart, Germany, and has been asexually reproduced repeatedly by vegetative cuttings over three generations. 'KLEDB10715' has been found to retain its distinctive characteristics through successive asexual propagations via vegetative cuttings.

No Plant Breeder's Rights have been applied for this variety. 'KLEDB10715' has not been made publicly available more than one year prior to filing of this application.

SUMMARY OF THE INVENTION

The following are the most outstanding and distinguishing characteristics of this new variety when grown under normal horticultural practices in hanging baskets in Stuttgart, Germany.

1. Very good branching;
2. Large flowers; and
3. Brilliant color.

DESCRIPTION OF PHOTOGRAPH

This new *Diascia* plant is illustrated by the accompanying photograph which shows the overall plant habit including blooms, buds, and foliage of the plant in full color. The colors shown are as true as can be reasonably obtained by conventional photographic procedures. The photograph was taken in the Summer of 2010 of twenty-seven week old plants grown from rooted cuttings in 15 centimeter baskets in Stuttgart, Germany under normal horticultural practices.

DESCRIPTION OF THE NEW VARIETY

The following detailed descriptions set forth the distinctive characteristics of 'KLEDB10715'. The data which define these characteristics were collected from asexual reproductions carried out in Stuttgart, Germany. The plant history was taken in the Summer of 2010 on twenty-seven week old plants grown in 15 centimeter baskets with a minimum pinch date of 9 weeks, and potting at week 10. Color readings were taken under natural light. Color references are primarily to The R.H.S. Colour Chart of The Royal Horticultural Society of London (R.H.S.), Fifth Edition (2007).

DESCRIPTION OF THE NEW PLANT

Classification:
- *Family*.—Scrophulariaceae.
- *Botanical name*.—*Diascia barberae* Hook.
- *Common name*.—*Diascia*.

Parentage:
- *Female parent*.—The proprietary *Diascia* plant, 'DB 2007 0101' (unpatented).
- *Male parent*.—The proprietary *Diascia* plant, 'DP1' (unpatented).

Growth:
- *Form and growth habit*.—Round compact.
- *Height*.—24.0 cm.
- *Width*.—50.0 cm.
- *Spread (including flowers)*.—50.0 cm.
- *Time to produce a finished flowering plant*.—6 weeks.
- *Outdoor plant performance*.—Very good after planting.
- *Time to initiate and develop roots*.—4 weeks.

Leaves:
- *Arrangement*.—Opposite.
- *Shape*.—Oval.
- *Apex*.—Obtuse.
- *Base*.—Cordate.
- *Margin*.—Serrate.

*Immature*.—Color: Green. Upper surface: RHS 143A. Lower surface: RHS 143B. Texture: Smooth.

*Mature* (*fully expanded*).—Length: 2.2 cm. Width: 1.4 cm. Color: Green. Upper surface: RHS 143A. Lower surface: RHS 143B.

*Venation*.—Type: Pinnate. Color: RHS 143A.

*Texture*.—Smooth.

*Petiole*.—Length: 0.6 cm. Width: 0.1 cm. Color: RHS 143C.

Stems:

*Length*.—30.0 cm.

*Diameter*.—0.2 cm.

*Color*.—RHS 143C.

*Texture*.—Smooth.

*Anthocyanin*.—Absent.

Flower bud:

*Shape*.—Oval.

*Diameter*.—0.6 cm.

*Length*.—0.5 cm.

*Color* (*at tight bud*).—RHS 60B.

Inflorescence:

*Inflorescence type*.—Terminal raceme with flowers in an alternate arrangement.

*Blooming habit*.—Continuous.

*Lastingness of individual blooms on the plant*.—3 to 4 days.

*Fragrance*.—Absent.

*Inflorescence length*.—5.5 cm.

*Peduncle*.—Color: RHS 143A. Length: 1.5 cm. Diameter: 0.1 cm. Texture: Smooth.

Flower:

*Type*.—Solitary.

*Quantity* (*per raceme*).—12 with usually 1 to 3 open at the same time.

*Shape*.—5 petals fused at base, 2 smaller upper petals fused, 2 lateral lobes and 1 broad lower lobe and 2 short spors at the underside formed by the lower ends of lateral and lower petals.

*Length*.—2.0 cm.

*Depth*.—0.3 cm.

*Width*.—1.5 cm.

*Color*.—Dark salmon. Upper surface: RHS 39B. Lower surface: RHS 39C. Corolla (inside color): RHS 39A.

*Petals* (*lobes*).—Quantity: 5. Arrangement: Fused and build typical flower shape with 2 long spurs at the back of the flower; flower is shaped with dropping lower lip and 4 small curly petals at top. Apex: Rounded. Base: Fused. Margin: Entire. Texture: Smooth.

*Upper lobes, size*.—Length (from the Corolla opening): 0.7 cm. Width: 0.7 cm.

*Lateral lobes, size*.—Length (from the Corolla opening): 0.6 cm. Width: 0.8 cm. Spur: Shape: Cuspidate. Length: 0.8 cm. Diameter: 0.2 cm. Color: RHS 60B.

*Lower lobe*.—Length (from the Corolla opening): 0.7 cm. Width: 1.3 cm.

*Sepals*.—Quantity: 5. Color: RHS 143A. Length: 0.3 cm. Width: 0.1 cm. Shape: Acuminate. Apex: Acute. Base: Obtuse. Anthocyanin: Absent. Texture: Smooth.

*Pedicels*.—Color: RHS 143A fading to RHS 199B. Length: 0.9 cm. Diameter: 0.05 cm. Texture: Smooth.

Reproductive organs:

*Stamens*.—Quantity: 4 coherent, arching forwards and somewhat twisting around the pistil. Filament: Color: RHS 59B. Length: 0.3 cm. Diameter: 0.05 cm. Anther color: RHS 14A. Pollen amount: Moderate. Pollen color: RHS 14A.

*Pistils*.—Quantity: 1. Length: 0.4 cm. Stigma color: RHS 143C. Style color: RHS 143C and RHS 199A.

Fruit and seed set: None observed.

COMPARISON WITH PARENTAL AND COMMERCIAL VARIETIES

'KLEDB10715' differs from the female parent, proprietary *Diascia* plant 'DB 2007 0101' (unpatented), in that 'KLEDB10715' has large dark salmon colored flowers, while 'DB 2007 0101' has medium sized pink colored flowers.

'KLEDB10715' differs from the male parent, proprietary *Diascia* plant 'DP1', (unpatented) in that 'KLEDB10715' has dark salmon colored flowers, while 'DP1' has pink colored flowers. Additionally, 'KLEDB10715' has very good branching, while 'DP1' has medium branching.

'KLEDB10715' differs from the commercial variety 'Darla Salmon' (unpatented) in that 'KLEDB10715' has salmon colored flowers, while 'Darla Salmon' has redder salmon colored flowers. Additionally, 'KLEDB10715' has better branching than 'Darla Salmon'.

We claim:

1. A new and distinct variety of *Diascia* plant named 'KLEDB10715' as shown and described herein.

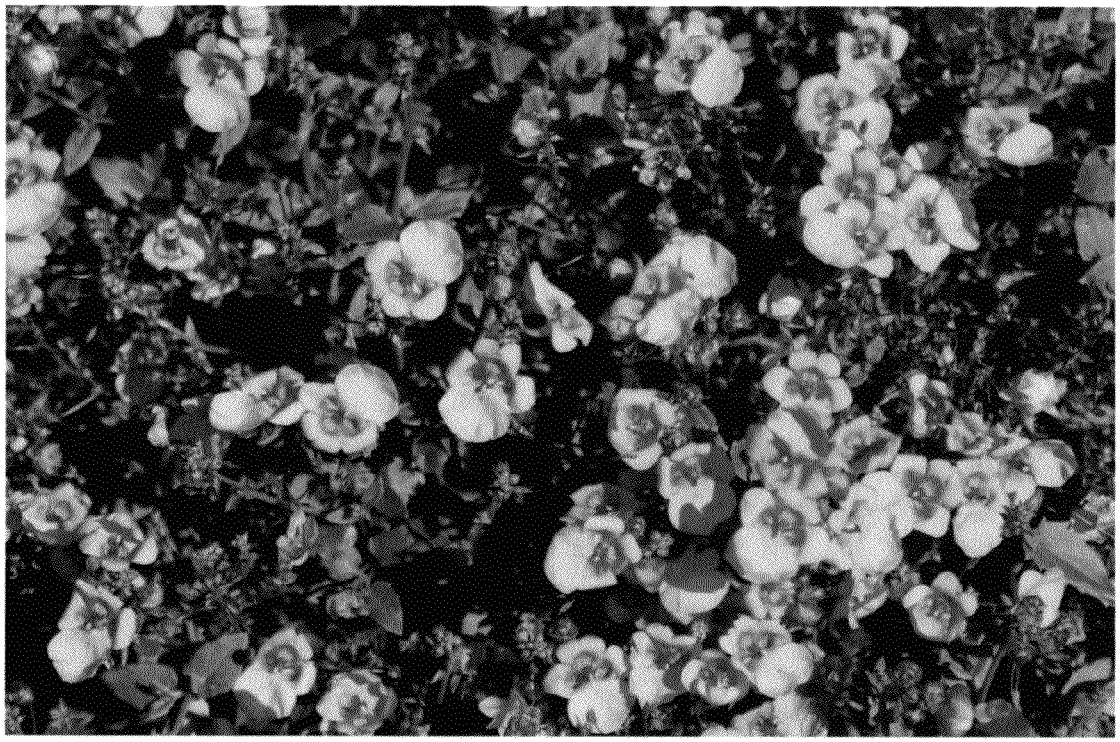

* * * * *